(12) United States Patent
Nishio

(10) Patent No.: US 7,347,324 B2
(45) Date of Patent: Mar. 25, 2008

(54) PACKAGED CONTAINER CONTAINING OCULAR PERFUSION/WASHING SOLUTION AND PROCESS FOR PRODUCING THE SAME

(75) Inventor: Mitsuhira Nishio, Himeji (JP)

(73) Assignees: Senju Pharmaceutical Co., Ltd., Osaka (JP); Otsuka Pharmaceutical Factory, Inc., Tokushima (JP)

( * ) Notice: Subject to any disclaimer, the term of this patent is extended or adjusted under 35 U.S.C. 154(b) by 308 days.

(21) Appl. No.: 10/522,681

(22) PCT Filed: Jul. 30, 2003

(86) PCT No.: PCT/JP03/09627

§ 371 (c)(1),
(2), (4) Date: Jan. 31, 2005

(87) PCT Pub. No.: WO2004/010918

PCT Pub. Date: Feb. 5, 2004

(65) Prior Publication Data

US 2006/0118433 A1 Jun. 8, 2006

(30) Foreign Application Priority Data

Jul. 30, 2002 (JP) .............................. 2002-221234

(51) Int. Cl.
*A61B 19/02* (2006.01)
(52) U.S. Cl. ...................... 206/438; 53/400; 53/434; 206/213.1; 604/408
(58) Field of Classification Search ............ 206/213.1, 206/219–220, 438, 568; 53/432–434, 455, 53/512, 400, 449; 424/715, 716; 604/403, 604/408–410
See application file for complete search history.

(56) References Cited

U.S. PATENT DOCUMENTS

| | | | | |
|---|---|---|---|---|
| 4,515,266 A | * | 5/1985 | Myers | ......................... 206/205 |
| 6,764,481 B1 | * | 7/2004 | Inada et al. | .................. 604/408 |
| 7,040,485 B2 | * | 5/2006 | Gupta et al. | ............. 206/484.1 |
| 7,047,708 B2 | * | 5/2006 | Inada et al. | .................... 53/400 |
| 2005/0126941 A1 | * | 6/2005 | Ferri et al. | ................... 206/323 |

FOREIGN PATENT DOCUMENTS

| | | | |
|---|---|---|---|
| JP | 11292151 | * | 10/1999 |
| JP | 2000-281147 | * | 10/2000 |

* cited by examiner

*Primary Examiner*—Luan K Bui
(74) *Attorney, Agent, or Firm*—Sughrue Mion, PLLC

(57) ABSTRACT

The present invention provides an improved packaged container containing an ocular perfusion/washing solution, the solution being securely prevented from generating gas bubbles that impede operation when used as an ocular perfusion/washing solution in cataract surgery, etc., and a process for producing the same. In the packaged solution container, the ocular perfusion/washing solution (1) is contained in a gas-permeable plastic container (2) which is packaged in a gas-impermeable packaging member (3). Between the container (2) and the packaging member (3), there is a space (4) which has a volume at least 4 times that of the total of the volume of the headspace of the container and the volume of dissolved gas. This space (4) holds a mixed gas atmosphere comprising carbon dioxide and helium and/or neon.

3 Claims, 1 Drawing Sheet

PACKAGED CONTAINER CONTAINING OCULAR PERFUSION/WASHING SOLUTION AND PROCESS FOR PRODUCING THE SAME

TECHNICAL FIELD

The present invention relates to a packaged container containing an ocular perfusion/washing solution and a process for producing the same.

BACKGROUND ART

"OPEGUARD™" (produced by Senju Pharmaceutical Co., Ltd. and sold by Takeda Chemical Industries, Ltd.) and "BSS PLUS™" (imported and sold by Santen Pharmaceutical Co., Ltd.) are representative commercially available solutions used for intraocular and extraocular perfusion and washing in ophthalmic surgeries such as cataract surgery, vitreous surgery and glaucoma surgery. Among ophthalmic surgeries using such an ocular perfusion/washing solution, a representative method for cataract surgery, phacoemulsification is carried out by ultrasonically disrupting a clouded crystalline lens and aspirating the same using a "phacoemulsifier".

More specifically, the surgery is carried out by breaking up a crystalline lens by mechanical impact (front-and-back vibrations) of a metal tip (such as an ultrasonic tip, a US tip, a phaco tip) that creates ultrasonic sound waves with the cavitation at the tip end, followed by aspirating the broken pieces of the lens through the tip, while a perfusate in an amount according to the amount of aspiration is supplied through a sleeve surrounding the tip so as to prevent the intraocular (anterior chamber) pressure from dropping due to the aspiration. Since the perfusate passes around such an US tip generating ultrasonic sound waves, numerous gas bubbles are generated in the solution due to the temperature rise and cavitation caused by the ultrasonic waves. The gas bubbles gather at the nodes in the standing wave and coalesce into large bubbles. When such bubbles are collapsed by the compressive force that acts on the solution, highly impactive acoustic energy is released into the solution and this energy transforms into shock waves, which act as part of the destructive force for disrupting the crystalline lens nucleus.

However, other gas bubbles that do not function as the above-mentioned force for destroying the nucleus but rather impair visibility around the tip region during the surgery may also occur, depending on the kind of perfusate used in the operation. That is, even when cavitation does not occur in the solution, the gas dissolved in the solution readily bubbles when the pressure drops below a certain level. Such gas bubbles do not generate acoustic energy high enough to produce a destructive force for disrupting the nucleus and rather impairs visibility during the surgery, thus having the disadvantage of impeding accurate visual inspection of the portion being operated on.

It is preferable that the perfusion/washing solution used in ophthalmic surgeries be prevented, as much as possible, from being accompanied by such bubbling that impairs visibility during the surgery.

DISCLOSURE OF INVENTION

An object of the invention is to provide an ocular perfusion/washing solution, and in particular, a packaged container containing an ocular perfusion/washing solution, which does not undergo bubbling that may impair visibility during ophthalmic surgeries.

The present inventors focused their attention on the bubbling that occurs in the use of perfusion/washing solutions (during ophthalmic surgeries) and impairs visibility, and carried out intensive research to inhibit or prevent such bubbling. During this research, the inventors found that the amount of generated gas bubbles varies not only depending on the apparatus used in the ophthalmic surgery and the apparatus operating conditions, but also according to the composition, production process and conditions of the perfusion/washing solution, kinds and amounts of gases dissolved in the solution, etc. Since many such divergent factors affect bubbling, the inventors considered it would be difficult to suppress the generation of gas bubbles to a level so as to not impede surgical operations by subjecting the ocular perfusion/washing solution to any particular treatment.

However, during their continued research, the inventors made the following surprising finding: in such a packaged, container containing an ocular perfusion/washing solution, when the volume of the interspace between the container and the packaging member is adjusted to a specific value and the interspace is filled with a mixed gas comprising carbon dioxide and at least one species selected from helium and neon, the obtained product is remarkably inhibited or prevented from bubbling upon use. The present invention has been accomplished based on this finding.

The present invention provides the inventions itemized below in items 1 to 5:

Item 1. A packaged container containing an ocular perfusion/washing solution, the solution being prevented from generating gas bubbles that impair visibility during ophthalmic surgery,
(1) the container being a gas-permeable plastic container;
(2) the container being packaged in a gas-impermeable packaging member;
(3) the interspace between the container and the packaging member has a volume which is at least 4 times that of the total of the volume of the headspace in the container and the volume of dissolved gas; and
(4) the interspace holds a mixed gas atmosphere of carbon dioxide and at least one species selected from helium and neon.

Item 2. The packaged container containing an ocular perfusion/washing solution according to item 1 wherein the mixed gas atmosphere consists of 80 to 99 vol. % of at least one species selected from helium and neon and 1 to 20 vol. % of carbon dioxide.

Item 3. The packaged container containing an ocular perfusion/washing solution according to item 1 wherein the volume of the gas dissolved in the solution contained in the container is 12 mL or less (25° C., 1 atm.) per liter of the solution.

Item 4. A process for producing a packaged container containing an ocular perfusion/washing solution, the solution being prevented from generating gas bubbles that impair visibility during ophthalmic surgeries, the process comprising the steps of:
(1) accommodating an ocular perfusion/washing solution in a gas-permeable plastic container;
(2) packaging the container in a gas-impermeable packaging member;
(3) adjusting the interspace between the container and the packaging member to a volume which is at least 4 times that of the total of the volume of the headspace in the container and the volume of dissolved gas; and (4) filling the interspace with a mixed gas of carbon dioxide and at least one species selected from helium and neon to hold the mixed gas atmosphere therein.

Item 5. The process according to item 4 wherein the mixed gas atmosphere consists of 80 to 99 vol. % of at least one species selected from helium and neon and 1 to 20 vol. % of carbon dioxide.

The present invention provides a packaged container containing an ocular perfusion/washing solution so as to prevent the solution from bubbling that impairs visibility during ophthalmic surgery. The packaged container containing an ocular perfusion/washing solution of the invention is characterized in that the solution does not undergo bubbling that may impair visibility during ophthalmic operations, such as cataract surgery, to thereby impede the operation.

The inventors found that the desired ocular perfusion/washing solution which is inhibited or prevented from bubbling can be produced by the above-mentioned method of the invention and, more specifically, can be obtained by: packaging a specific container in a specific packaging member; adjusting the volume of the interspace between the container and the packaging member to the above-mentioned specific level; and filling the space with a mixed gas of carbon dioxide and at least one species selected from helium and neon. The invention has been accomplished based on this finding.

Such specific bubbling-inhibitory and preventive effects achieved by the packaged container containing an ocular perfusion/washing solution of the invention are considered to be brought about for the following reason: the amount of gas dissolved in the ocular perfusion/washing solution in the packaged container of the invention is remarkably reduced compared to conventional packaged solution containers, and is presumably a major factor in bringing about such effects.

More specifically, when the interspace adjusted to the specific volume is filled with a mixed gas of helium or neon together with carbon dioxide as described above, the gas in the headspace of the container and the gas dissolved in the ocular perfusion/washing solution in the container pass through the container wall (gas-permeable plastic) into the interspace. For example, when an ocular perfusion/washing solution is accommodated in a container and the container is packaged in a packaging member according to standard production procedures, air exists in the interspace, the headspace of the container and the ocular perfusion/washing solution. As the interspace is filled (i.e., the air in the interspace is replaced) with a mixed gas containing helium gas, etc., the partial pressure of the air in the interspace decreases, so that the air in the headspace of the container and the ocular perfusion/washing solution passes through the container wall into the interspace. More specifically, the air dissolved in the ocular perfusion/washing solution is released from the solution and the container to the outside of the container until the partial pressures of air of the ocular perfusion/washing solution, the headspace of the container, and the interspace become equal. Although the helium or neon introduced into the interspace may pass through the container wall into the headspace of the container, these gases have significantly low solubility in the ocular perfusion/washing solution compared to air (oxygen, nitrogen, etc.), so that such gases hardly dissolve in the ocular perfusion/washing solution, thus reducing the amount of gas dissolved in the solution.

To ensure the stability of such a perfusion/washing solution, this type of packaged container may be produced in a nitrogen gas atmosphere. In this case, nitrogen gas is present in the interspace, the headspace of the container, and the ocular perfusion/washing solution in amounts according to the partial pressure. Nitrogen gas is effective in stabilizing the ocular perfusion/washing solution, i.e., preventing the solution from decomposing and deteriorating due to oxygen, but is ineffective, as in the case of air, in preventing the ocular perfusion/washing solution from bubbling when used. That is, as with air, nitrogen gas dissolves (is present) in the ocular perfusion/washing solution and thus cannot avoid the disadvantage of generating a marked amount of bubbling, according to the amount dissolved, during surgery.

A method of replacing such nitrogen by a mixed gas of carbon dioxide and helium and/or neon is also part of the invention. When the nitrogen in the interspace is replaced by a mixed gas of carbon dioxide and helium and/or neon according to the present invention, the nitrogen dissolved in the ocular perfusion/washing solution passes into the interspace, as in the case of air, but only a trace amount of helium and/or neon can dissolve in the ocular perfusion/washing solution compared to nitrogen, so that the amount of gas dissolved in the ocular perfusion/washing solution can be reduced to the desired level.

As described above, the packaged container of the invention is also characterized by reducing the volume of gas dissolved in the ocular perfusion/washing solution to a certain value or less. The present inventors have confirmed that in the packaged container containing an ocular perfusion/washing solution of the invention which is prevented from the bubbling that impairs visibility during ophthalmic surgery, the dissolved gas has a volume of 12 mL/L or less; and also confirmed that when the volume of dissolved gas is 12 mL/L or less, the desired bubbling-inhibitory and preventive effects of the invention are achieved.

In this specification, the volume of dissolved gas can be determined by, for example, measuring the concentrations of gases (oxygen, nitrogen, helium, neon, etc.) in the headspace of the container in an equilibrium state by a gasometric method such as gas chromatography (25° C., 1 atm.), followed by calculating from the gas volume ratios (partial pressures) the volume (mL) of each gas dissolved per liter of the solution. Since carbon dioxide does not influence bubbling as shown in the Experimental Example below, the volume of dissolved gas referred to herein is calculated without taking the volume of dissolved carbon dioxide into consideration. The volume of dissolved gas referred to herein denotes the amount (mL) of gas dissolved in the ocular perfusion/washing solution contained in the packaged container of the invention, and does not directly relate to the concentration (mL/L) of gas dissolved in the solution.

The packaged container of the invention allows an ocular perfusion/washing solution to be preserved in a stable manner over a long period of time without the risk of the active ingredients of the solution deteriorating with time. In addition, troubles, such as fracturing that packaged containers are likely to encounter when using glass bottles or the like, and defects of the product being heavy and inconvenient to handle can also be avoided. Furthermore, the packaged container has the advantage of easy manufacturing.

The packaged container of the invention is described below in more detail. The ocular perfusion/washing solution of the invention may be any known perfusion and/or washing solution. The ocular perfusion/washing solution of the invention contains, as essential components, bicarbonate ions (a compound that generates bicarbonate ions) and at least one species selected from oxyglutathione and dextrose.

The ocular perfusion/washing solution may further contain calcium ions and/or magnesium ions (compounds that release such ions). The composition of the solution may be a conventionally used composition or a slight modification thereof.

Examples of compounds that release bicarbonate ions in the ocular perfusion/washing solution include sodium hydrogen carbonate, ammonium hydrogen carbonate, potassium hydrogen carbonate, and other hydrogen carbonates. Such compounds are used in the form of aqueous solutions. Sodium carbonate, potassium carbonate and like carbonates that release or generate carbonate ions may also be used as compounds that release bicarbonate ions because aqueous solutions prepared by adding such compounds release bicarbonate ions in the pH range of the solutions. The bicarbonate ion concentration is not particularly limited, but is usually within the range of about 15-50 mM. This bicarbonate concentration corresponds to an aqueous bicarbonate solution concentration of about 0.1-0.4 w/v %. A bicarbonate concentration range of about 0.16-0.24 w/v % is particularly preferable.

Specific examples of compounds that release calcium ions or magnesium ions are chlorides, sulfates and the like of calcium and magnesium. When a compound that releases calcium ions or magnesium ions is included in the ocular perfusion/washing solution, the addition of a compound that releases citrate ions can securely prevent a reaction between the bicarbonate ions and calcium or magnesium ions co-existing in the obtained solution from precipitating calcium carbonate and/or magnesium carbonate. More specifically, citrate ions form chelates with calcium ions or magnesium ions, thus having the function of preventing these ions from directly combining with carbonate ions. Sodium citrate can be mentioned as a representative example of a compound that releases citrate ions. The amount of compound that releases citrate ions is preferably selected from the range of about 0.35-2 w/v %, and more preferably about 0.5-1.2 w/v %, calculated on the basis of the citrates.

The ocular perfusion/washing solution may have a general composition that contains the following components in the permissible ranges and optimal ranges shown below, per 1000 ml:

|  | Permissible range (g) | Optimal range (g) |
| --- | --- | --- |
| Oxyglutathione | 0-0.5 | 0-0.3 |
| Dextrose | 0.4-1.8 | 0.7-1.65 |
| Sodium hydrogen carbonate | 1.5-2.5 | 1.9-2.3 |
| Calcium chloride (as the anhydride) | 0.09-0.17 | 0.1-0.15 |
| Magnesium chloride or magnesium sulfate (as the anhydride). | 0.07-0.18 | 0.08-0.16 |

The ocular perfusion/washing solution may contain sodium chloride, potassium chloride and the like. The amount of sodium chloride is preferably within the range of about 0.5-0.9 w/v %, and particularly preferably about 0.6-0.8 w/v %. The amount of potassium chloride is preferably within the range of about 0.02-0.05 w/v %, and particularly preferably about 0.025-0.045 w/v %. The ocular perfusion/washing solution may further contain phosphate ions and ions of trace metals such as copper and zinc.

Of the above ocular perfusion/washing solutions, a solution containing at least one species selected from oxyglutathione and dextrose (hereinafter referred to as an "oxyglutathione solution") and a solution containing bicarbonate ions (hereinafter referred to as a "bicarbonate ion solution") may be independently prepared and separately accommodated in individual compartments of a gas-permeable plastic bag container comprising a plurality of intercommunicable compartments. Such forms of multiple compartment bags are already known in the field of parenteral infusion. Examples thereof are bags comprising a closure means for shutting the communication between two compartments (e.g. Japanese Examined Patent Publication No. 20550/1988, Japanese Examined Utility Model Publication No. 17474/1988), and a bag whose compartments are brought into communication by pressing the compartments to open a sealing portion therebetween (e.g. Japanese Unexamined Patent Publication Nos. 309263/1988 and 4671/1990). According to the present invention, the bicarbonate ion solution is enclosed in at least one of the compartments, and the oxyglutathione solution is enclosed in at least one of the other compartments.

In view of the stability of bicarbonate ions, the bicarbonate ion solution is preferably adjusted to a pH range of about 7.0-9.0, and particularly preferably about 7.0-8.5, using a pH adjusting agent such as sodium hydroxide, hydrochloric acid or the like. The solution may further contain a buffer such as sodium acetate or potassium acetate. The addition of such a buffer can prevent rapid pH changes. The concentration of such a buffer, for example, the concentration of sodium acetate, may be selected from the range of about 0.02-0.06 w/v %, and preferably about 0.03-0.05 w/v %.

To stably preserve oxyglutathione and/or dextrose, the oxyglutathione solution is preferably adjusted to a pH range of about 2.5-6.5, and particularly preferably about 3.0-6.0, using a pH adjusting agent such as those mentioned above. This solution also may contain a buffer having a buffering action such as sodium acetate, potassium acetate or the like.

In the packaged container of the invention, the gas-permeable plastic container for containing (enclosing, filling) the ocular perfusion/washing solution can be made of polyethylene, an ethylene-vinyl acetate copolymer, polypropylene, polyvinyl chloride or the like, or a resin mixture or laminate prepared by blending such above resin materials in a suitable proportion or laminating such resin materials. The container is not particularly limited in shape, size, thickness, etc., although rectangular bags are usually used. Generally, the bag preferably has an inner volume of about 20 mL to about 3 L and a thickness of about 100-500 μm.

According to the packaged container of the invention, the above gas-permeable plastic container containing an ocular perfusion/washing solution is packaged in a gas-impermeable packaging member. The term "gas-impermeable" referred to herein does not mean strictly impermeable to all gases but means that its permeability to gases, mainly to air (oxygen, nitrogen, etc.), carbon dioxide, helium, neon, etc. is relatively much lower than that of the container containing the ocular perfusion/washing solution (or solutions for preparation thereof). The same material as for the container may be used for a gas-impermeable packaging member of the invention merely by increasing its thickness. Preferable materials for the gas-impermeable packaging member are, for example, films or sheets comprising at least one member selected from the group consisting of polyethylene terephthalate (PET), polyethylene naphthalate (PEN), polyvinyl alcohol (PVA), ethylene-vinyl alcohol copolymers (EVOH), polyvinylidene chloride (PVDC), polyamides, polyethylene, cellophanes, polyacrylamides, cellulose resins, polyesters, polycarbonates, and polystyrene; films and sheets as above additionally having a vapor-deposited inorganic material such as silicon oxide or aluminum oxide on the surface; metal foils such as aluminum foil; and multiple-layer films or sheets prepared by laminating two or more types of such films or sheets or at least one such film or sheet and at least one metal foil (e.g., laminated films, aluminum films, aluminum laminated films, laminated sheets, aluminum sheets, aluminum laminated sheets, etc.).

The packaging member should have a shape and size appropriate for packaging the container therein. Generally, the packaged container of the invention is advantageously produced by a process comprising: producing a packaging member in the form of a bag by means of a suitable packaging apparatus such as a vertical 3-side sealing machine, a vertical pillow packaging machine, or a rotary packer; placing in the bag a container containing an ocular perfusion/washing solution; and sealing the bag containing the container. Therefore, the packaging member may have any suitable shape and size in accordance with such packaging procedures.

Examples of packaging members usable in the invention include those formed using a combination of two or more types of the above-mentioned films or sheets or at least one such film or sheet, and at least one other film or sheet, such as blister packs.

Examples of materials advantageously used for the gas-impermeable packaging members of the invention include laminates produced by further laminating an aluminum film or aluminum sheet on a laminated film or laminated sheet as mentioned above to enhance its gas-impermeability; laminates of two or more sheets of the above-mentioned aluminum film or aluminum sheet; double packages produced by packaging a laminated film packaging material in an aluminum film. When the gas-impermeable material packaging bag of the invention has a sufficiently ample sealing portion, permeation of gas through the seal can be prevented. Such an ample sealing portion is preferable in the packaged container of the invention.

The bag should have such a shape and size (inner volume) that the space between the container and packaging member formed by packaging the container in the packaging member has the specified volume. More specifically, since a specific amount of a mixed gas of carbon dioxide and helium gas and/or neon gas needs to be present in the interspace, the size and shape of the bag are determined so that the interspace has a sufficient volume for establishing the above-mentioned mixed gas atmosphere. The space needs to have a volume which is at least 4 times that of the total of the volume of the headspace in the container and the volume of dissolved gas. The volume is usually at least about 4, about 5, or about 6 times the total of the volume of the headspace in the container and the volume of dissolved gas, but not more than about 7, about 8, about 9 or about 10 times the total volume. To meet the above conditions, the bag preferably has a volume which is at least about 1.3 times, about 1.4 times or about 1.5 times as large as the volume of the container but not more than about 1.8 times, about 2.0 times, about 2.5 times or about 3 times that of the container.

According to the packaged container containing a perfusion/washing solution of the invention, providing the interspace with the specified volume and establishing a mixed gas atmosphere comprising carbon dioxide and helium and/or neon in the interspace are essential requirements. By meeting these requirements, the packaged container of the invention can control (reduce) the volume of gas dissolved in the ocular perfusion/washing solution to 12 mL or less per liter of the solution, thus securely preventing the occurrence of gas bubbles that impair visibility during ophthalmic surgery, i.e., the desired effect of the invention.

A method of filling the interspace with a mixed gas of carbon dioxide and helium and/or neon to establish the mixed gas atmosphere therein (a method of replacing the gas in the interspace by the mixed gas) can be mentioned as a representative means for establishing a mixed gas atmosphere of carbon dioxide and helium and/or neon in the space. More specifically, the method can be carried out by enclosing the container containing an ocular perfusion/washing solution in the packaging member in an atmosphere of the mixed gas. The method can also be carried out by filling the interspace with a mixed gas of carbon dioxide and helium and/or neon after the container containing an ocular perfusion/washing solution has been packaged in a packaging member by a vacuum-packaging technique, etc. The concentration of each gas in the mixed gas used in the above method is such that the total concentration of helium and neon is about 80 to about 99 vol. %, preferably about 85 to about 95 vol. %, more preferably about 90 to 93 vol. %, and particularly preferably about 91 to about 92 vol. %; and the concentration of carbon dioxide is about 1 to about 20 vol. %, preferably about 5 to about 15 vol. %, more preferably about 7 to about 10 vol. %, and particularly preferably about 8 to about 9 vol. %.

The production process for the packaged container of the invention may be the same as that used for a conventional packaged container of this type except that the process comprises the step of establishing a mixed gas atmosphere in the interspace (which may also be considered as a step of controlling the volume of dissolved gas). More specifically, the steps of filling and sterilizing the ocular perfusion/washing solution in the container, packaging the container in the packaging member, and sealing can be carried out according to the general procedures used in the production of similar kinds of containers and packaged containers, e.g., production techniques for injections.

The packaged container of the invention can be produced by not only the above methods but also by any suitable method that can control the volume of gas dissolved in the solution to the above-mentioned specific value or less.

The packaged container of the invention may additionally comprise various means known to stabilize ocular perfusion/washing solutions. For example, the packaged container may enclose a carbon dioxide-generating oxygen absorbent in the interspace (see, for example, Japanese Unexamined Patent Publications Nos. 1993-49675 and 1994-339512). It is also possible to accommodate in the interspace a pinhole detector capable of detecting pinholes, etc. in the packaging member (Japanese Unexamined Patent Publication No. 2000-28114), and/or a pH indicator capable of detecting the pH of the aqueous solution (Japanese Unexamined Patent Publication No. 1999-197215, EP1033124A2).

A preferable embodiment of the packaged container containing an ocular perfusion and/or washing solution of the invention is as shown in the accompanying drawing (FIG. 1). As shown in FIG. 1, the packaged container of the invention comprises a gas-permeable multiple compartment plastic bag (2) separately accommodating a bicarbonate ion solution and an oxyglutathione solution as ocular perfusion/washing solutions (1), (1) in compartments that are partitioned by a weakly sealed portion (6); a gas-impermeable packaging member (3) for packaging the bag; and an interspace (4) between the bag and the packaging member. The packaged container of the invention is characterized by having a specific amount of a mixed gas of carbon dioxide and helium and/or neon filling the interspace, so that the volume of the gas dissolved in the ocular perfusion/washing solution (1) can be controlled, thus preventing the occurrence of gas bubbles when the solution is used during ophthalmic surgery.

DESCRIPTION OF SYMBOLS

Figure 1:
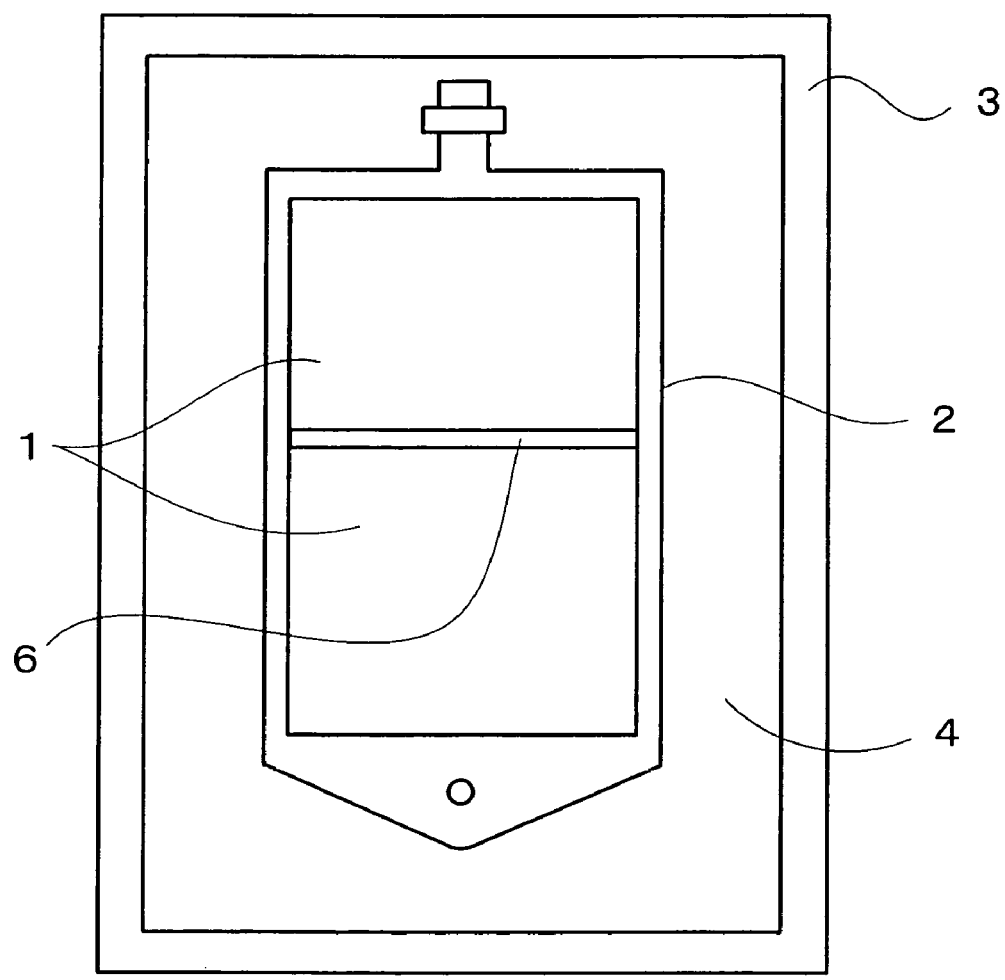
FIG. 1 is a schematic view illustrating a packaged bag containing an ocular perfusion/washing solution according to one embodiment of the invention.

1 Ocular perfusion/washing solution
2 Gas-permeable multiple compartment plastic bag
3 Gas-impermeable packaging member
4 Space between bag 2 and packaging member 3
6 Weakly sealed portion of gas-permeable multiple compartment plastic bag 2

BEST MODE FOR CARRYING OUT THE INVENTION

Production examples of packaged containers containing an ocular perfusion and/or washing solution of the invention and experimental examples using the obtained packaged containers are given below to describe the present invention in more detail.

EXAMPLE 1

A polyethylene plastic bag (thickness: about 260 μm) was prepared comprising two intercommunicable compartments (first and second compartments) separated from one another by a partition wall. The solutions described below were filled separately in the compartments, followed by sealing and sterilizing using a hot water shower. The obtained ocular solution bag was placed in a packaging pouch produced using a polyamide (nylon)/polyvinyl alcohol/polyethylene laminated film. After the air in the space between the bag and the pouch was evacuated, a mixed gas of helium and carbon dioxide (volume ratio of 91.5:8.5) was blown thereinto, followed by immediate sealing (space volume: about 400 mL), thus giving a packaged bag containing an ocular perfusion/washing solution.

<Solution Formulations>

(First compartment) An oxyglutathione solution containing the following components (total volume: 150 mL, headspace volume: 15 mL, pH: 4.5)

| | |
|---|---|
| Oxyglutathione | 0.09 g |
| Dextrose | 0.46 g |
| Sodium chloride | 3.32 g |
| Potassium chloride | 0.19 g |
| Sodium hydroxide | q.s. |
| Water for injection | to a total of 150 mL |

(Second compartment) A bicarbonate solution containing the following components (total volume: 350 mL, headspace volume: 35 mL, pH: 7.4)

| | |
|---|---|
| Sodium bicarbonate | 1.05 g |
| Sodium acetate trihydrate | 0.30 g |
| Sodium citrate dihydrate | 0.50 g |
| Calcium chloride dihydrate | 0.08 g |
| Magnesium sulfate hexahydrate | 0.10 g |
| Hydrochloric acid | q.s. |
| Water for injection | to a total of 350 mL |

Before packaging in the laminated film, the gas dissolved in the ocular perfusion/washing solution had a volume of about 9 mL. The volume of the space between the container and the packaging member (about 400 mL) was about 6.8 times that of the total (59 mL) of the volume of dissolved gas (9 mL) and the volumes of the headspaces of the container (15+35=50 mL).

EXAMPLE 2

A packaged bag containing an ocular perfusion and/or washing solution of the invention was prepared in a manner similar to Example 1, using the solutions described below in place of those used in Example 1.

(First compartment) An oxyglutathione solution containing the following components (total volume: 150 mL, headspace: 18 mL, pH: 4.5)

| | |
|---|---|
| Oxyglutathione | 0.09 g |
| Dextrose | 0.46 g |
| Calcium chloride dihydrate | 0.08 g |
| Magnesium sulfate hexahydrate | 0.10 g |
| Hydrochloric acid | q.s. |
| Sodium hydroxide | q.s. |
| Water for injection | to a total of 150 mL |

(Second compartment) A bicarbonate solution containing the following components (total volume: 350 mL, headspace: 38 mL, pH: 7.2)

| | |
|---|---|
| Sodium bicarbonate | 1.05 g |
| Sodium chloride | 3.57 g |
| Potassium chloride | 0.19 g |
| Disodium hydrogenphosphate dodecahydrate | 0.54 g |
| Hydrochloric acid | q.s. |
| Sodium hydroxide | q.s. |
| Water for injection | to a total of 350 mL |

Before packaging in the film, the volume of the gas dissolved in the ocular perfusion/washing solution was about 9 mL per bag. The volume of the space between the container and the packaging member (about 260 mL) was about 4 times that of the total (65 mL) of the volume of dissolved gas (9 mL) and the volumes of the headspaces of the container (18+38=56 mL).

EXAMPLE 3

A single compartment plastic container made of polyethylene (thickness: about 260 μm) was prepared. A 500 mL solution of the formulation shown below was placed in the compartment, followed by sealing and sterilizing using a hot water shower. The obtained ocular solution container was placed in a packaging pouch produced using a polyamide (nylon)/polyvinyl alcohol/polyethylene laminated film.

After the air in the space between the container and the packaging pouch was evacuated, a mixed gas of helium and carbon dioxide (91.5:8.5) was blown thereinto, followed by immediate sealing (space volume: about 400 ml), thus giving a packaged ocular solution bag of the invention.

<Solution Formulations>

| | |
|---|---|
| Dextrose | 0.75 g |
| Sodium bicarbonate | 1.05 g |
| Sodium chloride | 3.32 g |
| Potassium chloride | 0.18 g |
| Calcium chloride dihydrate | 0.09 g |
| Magnesium sulfate hexahydrate | 0.15 g |
| Hydrochloric acid | q.s. |
| Sodium hydroxide | q.s. |
| Water for injection | to a total of 500 ml |

Before packaging in the laminated film, the gases dissolved in the ocular solution had a volume of about 9 mL. The volume of the space between the container and the packaging pouch (about 400 mL) was about 8.2 times that of the total (49 mL) of the volume of dissolved gas (9 mL) and the volume of the headspace of the container (40 ml).

EXAMPLE 4

A packaged ocular solution bag of the invention was prepared in a manner similar to Example 1, using the solutions described below in place of those used in Example 1.

<Solution Formulations>

(First compartment) An oxyglutathione solution containing the following components (total volume: 150 mL, headspace: 18 mL, pH: 4.0 to 5.0)

| | |
|---|---|
| Oxyglutathione | 0.09 g |
| Dextrose | 0.46 g |
| Sodium chloride | 0.995 g |
| Potassium chloride | 0.19 g |
| Hydrochloric acid | q.s. |
| Sodium hydroxide | q.s. |
| Water for injection | to a total of 150 mL |

(Second compartment) A bicarbonate solution containing the following components (total volume: 350 mL, inner headspace: 38 mL, pH: 7.3 to 8.3)

| | |
|---|---|
| Sodium bicarbonate | 1.05 g |
| Sodium chloride | 2.32 g |
| Sodium acetate trihydrate | 0.30 g |
| Sodium citrate dihydrate | 0.50 g |
| Calcium chloride dihydrate | 0.08 g |
| Magnesium chloride hexahydrate | 0.10 g |
| Hydrochloric acid | q.s. |
| Sodium hydroxide | q.s. |
| Water for injection | to a total of 350 mL |

Before packaging in the film, the volume of the gas dissolved in the ocular solution was about 9 mL per bag. The volume of the space between the container and the packaging member (about 260 mL) was about 4 times that of the total (65 mL) of the volume of dissolved gas (9 mL) and the volumes of the headspaces of the container (18+38=56 ml).

EXAMPLE 5

A packaged ocular solution bag of the invention was prepared in a manner similar to Example 1, using the solutions described below in place of those used in Example 1.

<Solution Formulations>

(First compartment) An oxyglutathione solution containing the following components (total volume: 150 mL, headspace: 18 mL, pH: 4.0 to 5.0)

| | |
|---|---|
| Oxyglutathione | 0.09 g |
| Dextrose | 0.46 g |
| Sodium chloride | 0.995 g |
| Calcium chloride dihydrate | 0.08 g |
| Magnesium chloride hexahydrate | 0.10 g |
| Hydrochloric acid | q.s. |
| Sodium hydroxide | q.s. |
| Water for injection | to a total of 150 mL |

(Second compartment) A bicarbonate solution containing the following components (total volume: 350 mL, inner headspace: 38 mL, pH: 7.3 to 8.3)

| | |
|---|---|
| Sodium bicarbonate | 1.05 g |
| Sodium chloride | 2.32 g |
| Potassium chloride | 0.19 g |
| Disodium hydrogenphosphate dodecahydrate | 0.54 g |
| Hydrochloric acid | q.s. |
| Sodium hydroxide | q.s. |
| Water for injection | to a total of 350 mL |

Before packaging in the film, the volume of the gas dissolved in the ocular solution was about 9 mL per bag. The volume of the space between the container and the packaging member (about 260 mL) was about 4 times that of the total (65 mL) of the volume of dissolved gas (9 mL) and the volumes of the headspaces of the container (18+38=56 ml).

EXAMPLE 6

Packaged ocular solution bags of the invention were prepared in a manner similar to Examples 1, 2, 3, 4 and 5, using as a packaging member an aluminum film (cellophane/aluminum foil/polyethylene) in place of the laminated film used in Example 1, 2, 3, 4 or 5.

EXAMPLE 7

A packaged ocular solution bag of the invention is prepared that has an interior transparent window (size: 8×6 cm) produced using a laminated film (polyamide(nylon)/silicon oxide vapor-deposited on polyvinyl alcohol/polyethylene) in part of the aluminum film packaging member of the packaged ocular solution bag obtained in Example 6.

EXAMPLE 8

A packaged ocular solution bag of the invention whose interior can be visually inspected by peeling off an aluminum film before opening the package is prepared by firmly affixing an aluminum film (cellophane/aluminum foil) to the transparent window portion of the laminated film packaging member of the packaged ocular solution bag obtained in Example 7.

EXAMPLE 9

Double-packaged ocular solution bags of the invention are prepared by packaging a packaged ocular solution bag obtained in Example 1, 2, 3, 4 or 5 in an aluminum film (cellophane/aluminum foil/polyethylene) and evacuating the air from between the laminated film package and the aluminum package, followed by sealing.

EXAMPLE 10

Packaged ocular solution bags of the invention are prepared in a manner similar to Examples 1, 2, 3, 4 and 5, using as a packaging member a film comprising a laminated film (polyamide(nylon)/silicon oxide vapor-deposited on polyvinyl alcohol/polyethylene) on one side and an aluminum film (cellophane/aluminum foil/polyethylene) on the other in place of the laminated film used in Example 1, 2, 3, 4 or 5.

EXAMPLE 11

A packaged ocular solution bag of the invention is prepared in a manner similar to Example 6, using an aluminum film (polyamide(nylon)/aluminum foil/polyethylene/aluminum foil/polypropylene) as the packaging material in place of the aluminum film used in Example 6.

EXPERIMENTAL EXAMPLE 1

A test was carried out to investigate whether or not the ocular perfusion/washing solution in the packaged container of the invention bubbles to a degree that impairs visibility during surgery, when used in a phacoemulsification system for cataract treatment.

A control sample containing the specified amount of air in the space between the container and the packaging member was prepared.

A sample of the invention was prepared by evacuating the specified amount of air from the space between the container and the packaging member using a syringe and replacing it with the same amount of a mixed gas of helium and carbon dioxide.

More specifically, a packaged container was prepared according to Example 1 and the gas (about 400 mL) in the interspace between the container and the packaging member was evacuated using a 500 mL gas syringe and then about 400 mL of helium gas (100%) was introduced into the space using the same syringe. The gas (about 400 mL) in the space was similarly evacuated and 385 mL of helium gas (100%) and 16 mL of carbon dioxide gas (100%) were then introduced simultaneously using, respectively, the previous syringe and a different gas syringe, followed by sealing the opening, thus giving a sample of the invention in which the interspace had a mixed gas atmosphere (with a volume about 7 times that of the total volume of the headspace of the container and the dissolved gas).

A positive control sample was prepared by mixing first and second compartment solutions having the formulations shown in Example 1 and placing the mixture in a 700 mL glass vial (hermetic container), followed by sealing while reducing the pressure by 750 mmHg (vacuum sealing) and introducing 6 mL of carbon dioxide gas into the headspace of the vial using a gas syringe.

With respect to the control sample and the sample of the invention (11 days after preparation, i.e., after the atmosphere in the headspace of the container had reached equilibrium with the dissolved gas), gas was sampled from the headspace of each container using a gas tight syringe, and 1 mL of each gas sample was injected into a gas chromatograph (GC-14A, product of Shimazu Corporation). The concentrations of oxygen, nitrogen and helium were determined with reference to a calibration curve obtained using a standard gas and their volume ratios (partial pressures) were calculated. Gas chromatography conditions were as follows:

Detector: TCD
Carrier gas: Argon
Column packing material: Molecular Sieve 13X-S
Column temperature: 50° C.
Injection gas volume: 1 mL The total concentration of dissolved oxygen, nitrogen and helium was calculated from the partial pressure and solubility of each gas.

As a result, the total concentration of dissolved gases (air) in the control sample was about 15.8 mL/L, and that in the sample of the invention was about 11 mL/L (reduced to about 60% of the control sample).

Since the positive control was in a reduced pressure state in the vial, its gas concentration was not determined.

The control sample, the sample of the invention and the positive control sample were tested with respect to the following:

(1) Bubbling Test

A bubbling test was carried out using the following apparatus and conditions:

(1-1) Apparatus: Allergan Inc.'s Phacoemulsification System for Cataracts (Sovereign™)

(1-2) Tip: Phaco Pack, AMO LAMINAR™ Flow Phaco, Tip30°

(1-3) Vacuum Conditions:
Flow rate: 20 mL/min
Maximum vacuum pressure: 300 mmHg (1-4) Ultrasonic Intensity: the Following 3 Intensities were used.
Intensity 30%: (general conditions)
Intensity 50%: (the maximum intensity actually used for the disruption of a hard crystalline lens or like object.
Intensity 100%: (the machine's maximum intensity)

(1-5) Ultrasound Duration: for 30 Seconds (1-6) Method of Observing Bubbling:

The ocular perfusion/washing solution of each sample (prepared by mixing the first and second compartment solutions in the case of the control sample and the sample of the invention) was placed in a glass dish and a tip end was immersed in the solution to generate ultrasound waves. The occurrence of bubbling was visually observed. The degree of bubbling at the above 3 levels of ultrasonic intensity was evaluated according to the following criteria:

−; no bubbling
+; a small amount of bubbling occurred intermittently without causing any visibility problems.
++; bubbling occurred continuously, so that it would be somewhat difficult to observe the tip end during ophthalmic surgery.
+++; bubbling occurred continuously, so that it would be difficult to observe the tip end during ophthalmic surgery.

(2) Evaluation of pH and the Amount of Carbon Dioxide

Each sample was stored at room temperature for 11 days and the pH and the amount of carbon dioxide ($CO_2$) of the ocular perfusion/washing solution (prepared by mixing the first and second compartment solutions in the case of the control sample and the sample of the invention) were then determined. Tests were carried out using 3 specimens per sample, followed by calculating the mean of the 3 specimens.

The amount of carbon dioxide was measured by gas chromatography after adding sulfuric acid to each specimen to convert bicarbonate ions in the specimens to carbon dioxide.

(3) Results

The results of the above test items are shown below in Table 1 (bubbling test), Table 2 (pH) and Table 3 (carbon dioxide amount).

For comparison, Table 1 includes the results of the same tests using physiological saline in a commercially available plastic polypropylene bottle (concentration of dissolved gas: 18.6 mL/L, presumed to be close to saturation).

TABLE 1

| Ocular perfusion/washing solution | Ultrasonic intensity | | |
|---|---|---|---|
| | 20% | 50% | 100% |
| Sample of the invention | − | − | − |
| Control sample | − | + | ++ |
| Commercially available physiological saline | + | ++ | +++ |
| Positive control sample | − | − | − |

TABLE 2

| Ocular perfusion/washing solution | pH | | | |
|---|---|---|---|---|
| | 1 | 2 | 3 | Mean |
| Sample of the invention | 7.48 | 7.50 | 7.48 | 7.49 |
| Control sample | 7.50 | 7.51 | 7.53 | 7.51 |
| Positive control sample | 7.51 | 7.50 | 7.52 | 7.51 |

TABLE 3

| Ocular perfusion/washing solution | Carbon dioxide amount (mmol/L) | | | |
|---|---|---|---|---|
| | 1 | 2 | 3 | Mean |
| Sample of the invention | 26.3 | 25.8 | 25.5 | 25.9 |
| Control sample | 25.3 | 25.4 | 24.8 | 25.2 |
| Positive control sample | 25.6 | 25.3 | 26.0 | 25.6 |

The results of Tables 1, 2 and 3 clearly show the following:

Comparing the sample of the invention and the control sample, the control sample had an evaluation of + at an ultrasonic intensity of 50% (++ at an ultrasonic intensity of 100%)(i.e., bubbling occurred), whereas the sample of the invention had no bubbling problems at any ultrasonic intensity. This demonstrates that, as with the positive control sample prepared by filling a hermetic container under a reduced pressure, the sample of the invention is securely prevented from bubbling (see Table 1).

Comparing the sample of the invention, control sample and positive control sample, none of the samples showed a substantial change in pH of the ocular perfusion/washing solution. It is thus considered that filling of the mixed gas of helium and carbon dioxide is not accompanied by adverse effects such as quality deterioration of the ocular perfusion/washing solution (see Table 2).

Furthermore, the sample of the invention, the control sample and the positive control sample had no differences in the amount of carbon dioxide in the solution. This indicates that the amount of carbon dioxide does not influence the occurrence of bubbling.

INDUSTRIAL APPLICABILITY

The packaged container containing an ocular perfusion/washing solution of the invention is characterized by lack of bubbling that may impair an operator's vision during ophthalmic operations, such as cataract surgery, and impede the operation. Therefore, the packaged solution container can be advantageously used in ophthalmic surgery.

The invention claimed is:

1. A packaged container containing an ocular perfusion/washing solution, the solution being prevented from generating gas bubbles that impair visibility during ophthalmic surgery,
    (1) the container being a gas-permeable plastic container;
    (2) the container being packaged in a gas-impermeable packaging member;
    (3) the packaged container comprising an interspace between the gas-permeable plastic container and the packaging member, wherein the interspace has a volume which is at least 4 times that of the total of a volume of headspace in the container and a volume of dissolved gas; and
    the interspace holds a mixed gas atmosphere of carbon dioxide and at least one species selected from helium and neon wherein the mixed gas atmosphere consists of 80 to 99 vol. % of at least one species selected from helium and neon and 1 to 20 vol. % of carbon dioxide.

2. A packaged container containing an ocular perfusion/washing solution, the solution being prevented from generating gas bubbles that impair visibility during ophthalmic surgery,
    (4) the container being a gas-permeable plastic container;
    (5) the container being packaged in a gas-impermeable packaging member;
    (6) the packaged container comprising an interspace between the gas-permeable plastic container and the packaging member, wherein the interspace has a volume which is at least 4 times that of the total of a volume of headspace in the packaged container and a volume of dissolved gas; and
    the interspace holds a mixed gas atmosphere of carbon dioxide and at least one species selected from helium and neon wherein the volume of the gas dissolved in the solution contained in the container is 12 mL or less (25° C., 1 atm.) per liter of the solution.

3. A process for producing a packaged container containing an ocular perfusion/washing solution, the solution being prevented from generating gas bubbles that impair visibility during ophthalmic surgeries,
    the process comprising the steps of:
    (1) accommodating an ocular perfusion/washing solution in a gas-permeable plastic container;
    (2) packaging the container in a gas-impermeable packaging member wherein the packaged container comprises an interspace between the gas-permeable plastic container and the packaging member;

(3) adjusting the interspace between the gas-permeable plastic container and the packaging member, wherein the interspace has a volume which is at least 4 times that of the total of a volume of headspace in the packaged container and a volume of dissolved gas; and filling the interspace with a mixed gas of carbon dioxide and at least one species selected from helium and neon to establish the mixed gas atmosphere therein wherein the mixed gas atmosphere consists of 80 to 99 vol. % of at least one species selected from helium and neon and 1 to 20 vol. % of carbon dioxide.

* * * * *